United States Patent
Maggio

(10) Patent No.: US 10,596,468 B2
(45) Date of Patent: Mar. 24, 2020

(54) METHOD AND SYSTEM FOR DEPLOYMENT OF STANDALONE AND REACTIVE SQUARES GAMES ADAPTED FOR EMPLOYMENT IN A FANTASY SPORTS LEAGUE ENVIRONMENT

(71) Applicant: Frank S. Maggio, Pinellas Park, FL (US)

(72) Inventor: Frank S. Maggio, Pinellas Park, FL (US)

( * ) Notice: Subject to any disclaimer, the term of this patent is extended or adjusted under 35 U.S.C. 154(b) by 0 days.

(21) Appl. No.: 15/232,834

(22) Filed: Aug. 10, 2016

(65) Prior Publication Data

US 2016/0346673 A1   Dec. 1, 2016

Related U.S. Application Data

(63) Continuation-in-part of application No. 14/852,477, filed on Sep. 11, 2015, now Pat. No. 9,858,764.
(Continued)

(51) Int. Cl.
*A63F 13/61* (2014.01)
*A63F 13/25* (2014.01)
(Continued)

(52) U.S. Cl.
CPC .............. *A63F 13/61* (2014.09); *A63F 13/20* (2014.09); *A63F 13/25* (2014.09); *A63F 13/46* (2014.09);
(Continued)

(58) Field of Classification Search
CPC ........ A63F 3/0615; A63F 13/20; A63F 13/25; A63F 13/46; A63F 13/61; A63F 13/828;
(Continued)

(56) References Cited

U.S. PATENT DOCUMENTS

2007/0102877 A1   5/2007   Personius et al.
2007/0270202 A1*  11/2007  Vostoris ........................ 463/16
(Continued)

OTHER PUBLICATIONS

"How to Play Football Squares", dated Nov. 3, 2013, https://web.archive.org/web/20131103095352/http://www.superbowlsquares.org:80/how-to-play-football-squares.php.*
(Continued)

*Primary Examiner* — Allen Chan
(74) *Attorney, Agent, or Firm* — TannerIP PLLC; Daniel A. Tanner, III; James E. Golladay, II

(57) ABSTRACT

A system and method are provided for implementing a uniquely automated, and otherwise gamified, version of a Squares Game. The disclosed schemes incorporate technology for hosting on, or interacting/reacting with, potential participants' mobile and personal communicating and computing devices. The disclosed systems and methods uniquely adapt the gamified Squares Game to implement hybrid schemes employed by one or more of the myriad "fantasy sports" leagues that have become attractive to mass audiences. The disclosed schemes provide event-long score tabulation as a mechanism by which to allocate awards. The disclosed schemes provide for branding to certain sponsors of a Super Squares event, league, or season, in a manner that the a sponsoring entity's retail and/or website properties may be linked to the automated game in order to facilitate increased traffic, sales and/or exposure.

12 Claims, 4 Drawing Sheets

Related U.S. Application Data

(60) Provisional application No. 62/051,931, filed on Sep. 17, 2014, provisional application No. 62/049,329, filed on Sep. 11, 2014.

(51) Int. Cl.
*A63F 13/46* (2014.01)
*A63F 13/20* (2014.01)
*A63F 13/828* (2014.01)
*A63F 13/65* (2014.01)
*A63F 13/812* (2014.01)
*C07D 401/14* (2006.01)
*G07F 17/32* (2006.01)
*C07D 215/46* (2006.01)
*C07D 401/12* (2006.01)

(52) U.S. Cl.
CPC ............ *A63F 13/65* (2014.09); *A63F 13/812* (2014.09); *A63F 13/828* (2014.09); *C07D 215/46* (2013.01); *C07D 401/12* (2013.01); *C07D 401/14* (2013.01); *G07F 17/3272* (2013.01); *G07F 17/3288* (2013.01)

(58) Field of Classification Search
CPC .... A63F 13/65; A63F 13/812; G07F 17/3272; G07F 17/3288

USPC .......................................................... 463/17
See application file for complete search history.

(56) References Cited

U.S. PATENT DOCUMENTS

| | | |
|---|---|---|
| 2009/0005165 A1 | 1/2009 | Arezina et al. |
| 2009/0005175 A1 | 1/2009 | Rosenau et al. |
| 2009/0181738 A1* | 7/2009 | Costin ................ A63F 13/12 463/4 |
| 2012/0208620 A1 | 8/2012 | Schugar |
| 2014/0274332 A1 | 9/2014 | Carlin |
| 2015/0032519 A1* | 1/2015 | Brooks ............ G06Q 30/0209 705/14.12 |
| 2015/0080124 A1 | 3/2015 | Andersen et al. |
| 2015/0179021 A1 | 6/2015 | Alexander |
| 2015/0325085 A1 | 11/2015 | O'Hagan |
| 2016/0078715 A1 | 3/2016 | Igt |
| 2016/0078729 A1 | 3/2016 | Maggio |

OTHER PUBLICATIONS

International Search Report for PCT/US2017/046384 dated Nov. 2, 2017.
Written Opinion for PCT/US2017/046384 dated Nov. 2, 2017.

* cited by examiner

METHOD AND SYSTEM FOR DEPLOYMENT OF STANDALONE AND REACTIVE SQUARES GAMES ADAPTED FOR EMPLOYMENT IN A FANTASY SPORTS LEAGUE ENVIRONMENT

This application is a Continuation-in-Part of U.S. patent application Ser. No. 14/852,477, entitled "Methods and Systems for Deployment of Standalone and Reactive Squares Games" by Frank S. Maggio, filed in the U.S. Patent and Trademark Office on Sep. 11, 2015, which issued as U.S. Pat. No. 9,858,764 on Jan. 2, 2018, and which in turn claims priority to U.S. Provisional Patent Application No. 62/049,329 entitled "Method And System For Deployment Of Standalone And Reactive Sport-Related Game Squares Games" by Frank S. Maggio, filed in the U.S. Patent and Trademark Office on Sep. 11, 2014, and to U.S. Provisional Patent Application No. 62/051,931 entitled "Method And System For Deployment Variants Of Standalone And Reactive Sport-Related Game Squares Games" by Frank S. Maggio, filed in the U.S. Patent and Trademark Office on Sep. 17, 2014, the disclosures of which are hereby incorporated by reference herein in their entirety.

BACKGROUND

1. Field of the Disclosed Embodiments

This disclosure relates to systems and methods for uniquely adapting an automated and otherwise gamified Squares Game, which may be hosted on mobile and personal communicating and computing devices, to implement hybrid methods and systems employed by one or more of the myriad "fantasy sports" leagues that have become attractive to mass audiences.

2. Related Art

An extremely popular game played by sports fans, including attendees and viewers of particularly noteworthy football games, including what is commonly referred to as the Big Game, is the "Squares Game." FIG. 1 schematically illustrates a typical embodiment of a Squares Game matrix form 100. In popular embodiments, a ten by ten square matrix participation area 110 is hand-drawn or otherwise produced by a host. The host circulates the matrix form 100 among colleagues, associates, friends, co-workers, customers and the like soliciting their participation in the game. The matrix form 100 may include certain logos, other identifying information, contact data, instructions or other like inputs in, for example, a free form identifying field 160. The matrix form 100 may contain blank border fields 120,130 outside the ten by ten square matrix participation area 110, e.g., across the top (as show) or bottom, and down the left side (as shown) or right side, to be filled in when all of the hundred squares in the matrix participation area 110 have been selected by participants.

For the host, the process of soliciting participation in filling in the matrix participation area 110 by "selling" the squares, one square or a couple of squares at a time, can be a time-consuming and frustrating undertaking as enthusiasm for participation among a narrow population of participants with whom the host may be associated and/or interact ebbs and flows. Some of this burden on the host may be eased by "selling" the individual squares in pre-planned groups of four (as is indicated in FIG. 1 by the slightly heavier lines in the matrix participation area 110) as, for example, "super" squares.

After selling/filling all of the squares in the matrix participation area 110, the still blank border fields 120,130, may be filled in with "score heading" numbers in the manner shown in FIG. 1. These score heading numbers, in the context of a conventional football pool, corresponding to the final digit of each of the "Home" and "Away" (see elements 140,150) team scores for the game, or at intervals, e.g., by halves or by quarters, according to a pre-determined and pre-announced prize structure. The score heading numbers entered into the border fields 120,130 are typically randomly selected one at a time, and placed at the top or left of a column or row in the example shown in FIG. 1, respectively.

The letters A-Z (minus Q) will be described in view of the disclosed embodiments below.

Participants in Squares Games may, for example, pay $5 per square, for a total prize pool of $500. The collected sales proceeds from the Squares Game are then divided among the participants, typically based upon the score of the game at the pre-determined intervals. As examples, the score at the end of each quarter of a football game may garner the "winning" participant a 25% increment of the overall prize pool, or these scores may garner 20% increments for the first 3 quarters, and 40% for the end of game score. In some instances, the Squares Game host or organizer may retain a portion of the square sales proceeds, to offset a "cost" of managing the game. These games are generally informally administered among groups of friends and/or colleagues, and the "rules" are generally pre-briefed to all participants who then voluntarily agree to participate according to those rules.

SUMMARY OF THE DISCLOSED EMBODIMENTS

As is mentioned above there are many variations on this general theme and in the establishment of the matrix participation area 110 as shown in the exemplary embodiment illustrated in FIG. 1, all of which are pre-established and explained to the participants. Further, the concept although generally associated with football games may be adjusted and adaptable to other sports, in many unique ways.

With the proliferation of individual mobile communicating and computing devices, an opportunity exists to substantially automate a conventional Squares Game in a manner that increases user participation and interest and to incorporate participation in such games on a local, regional or broader scope into an overall reactive advertising scheme in which participants may be rewarded, not only for their participation in a particular game, but more broadly for their participation in a reactive advertising environment overall.

In view of the above background, it may be advantageous to find some manner by which to automate a conventional Squares Game in a manner that achieves the above advanced objectives. In this regard, it may be particularly advantageous to provide programming for individual users' mobile communicating and computing ("smart") devices that may facilitate their employment to rewarding, challenging and interesting automated gamification of, and reactive advertising associated with, a Squares Game. An objective may be to employ the automated Squares Game as an entry into a reactive advertising scheme thereby generating, or otherwise stimulating, a new degree of interest in integrated commercial and advertising content.

Exemplary embodiments of the systems and methods according to this disclosure may provide unique automation of a Squares Game for participation across a broader spectrum of a participant population.

Exemplary embodiments may implement automated schemes that are directed at overcoming the burden of hosting a local Squares Game in a limited participant population environment.

Exemplary embodiments may ease the logistical burden on any host of a Squares Game in at least one of automating the selling of the squares, selecting of the numbers, and preparing of the finalized matrices to be automatically distributed to all participants prior to the event to which the Squares Game is linked.

Exemplary embodiments may distribute participation across a broader user population than simply the potential participants, e.g., 100 or so people, that the host knows.

Exemplary embodiments may verify receipt of the finalized matrices with all of the participants in order to ensure that attention remains high. It is recognized that some participants' interest in the particular sporting event with which a Squares Game may be associated is specifically increase based on their vested interest in the outcome of each prize distributing interval. Part of the allure of Squares Games is that they add excitement to sporting events, particularly when a favored team is not winning, or when the game is no longer close.

Exemplary embodiments may provide automated notifications to winners of particular Squares Games, all of whom will not be viewing the sporting event together.

Exemplary embodiments may execute an automated randomization scheme for selecting the numbers to fill the border areas in a manner that reduces any possibility for controversy with the host based on the ultimately selected numbering scheme.

Exemplary embodiments may collect participant information for recurring gaming or to separately solicit participation in reactive advertising that may be of interest to the participants based on the information that they provide.

Exemplary embodiments may implement hybrid methods and systems used by myriad "fantasy sports" leagues by providing, for example, event-long score tabulation as another mechanism by which to allocate awards.

Exemplary embodiments may provide for branding to certain sponsors of a Super Squares event, league, or season, in a manner that the a sponsoring entity's retail and/or website properties may be linked to the automated game in order to facilitate increased traffic, sales and/or exposure. In embodiments, an involvement of sponsoring entities may contribute to increased funding for prizing, which may result, in turn, in increased user attraction and participation leading to increasing revenues realized by a hosting entity and/or related parties.

These and other features, and advantages, of the disclosed systems and methods are described in, or apparent from, the following detailed description of various exemplary embodiments.

BRIEF DESCRIPTION OF THE DRAWINGS

Various exemplary embodiments of the systems and methods for uniquely adapting an automated and otherwise gamified Squares Game, which may be hosted on mobile and personal communicating and computing devices, to implement hybrid methods and systems employed by one or more of the myriad "fantasy sports" leagues that have become attractive to mass audiences, with application across many sporting events and sports types, according to this disclosure, will be described, in detail, with reference to the following drawings, in which.

DETAILED DESCRIPTION OF EMBODIMENTS

Figure 1:
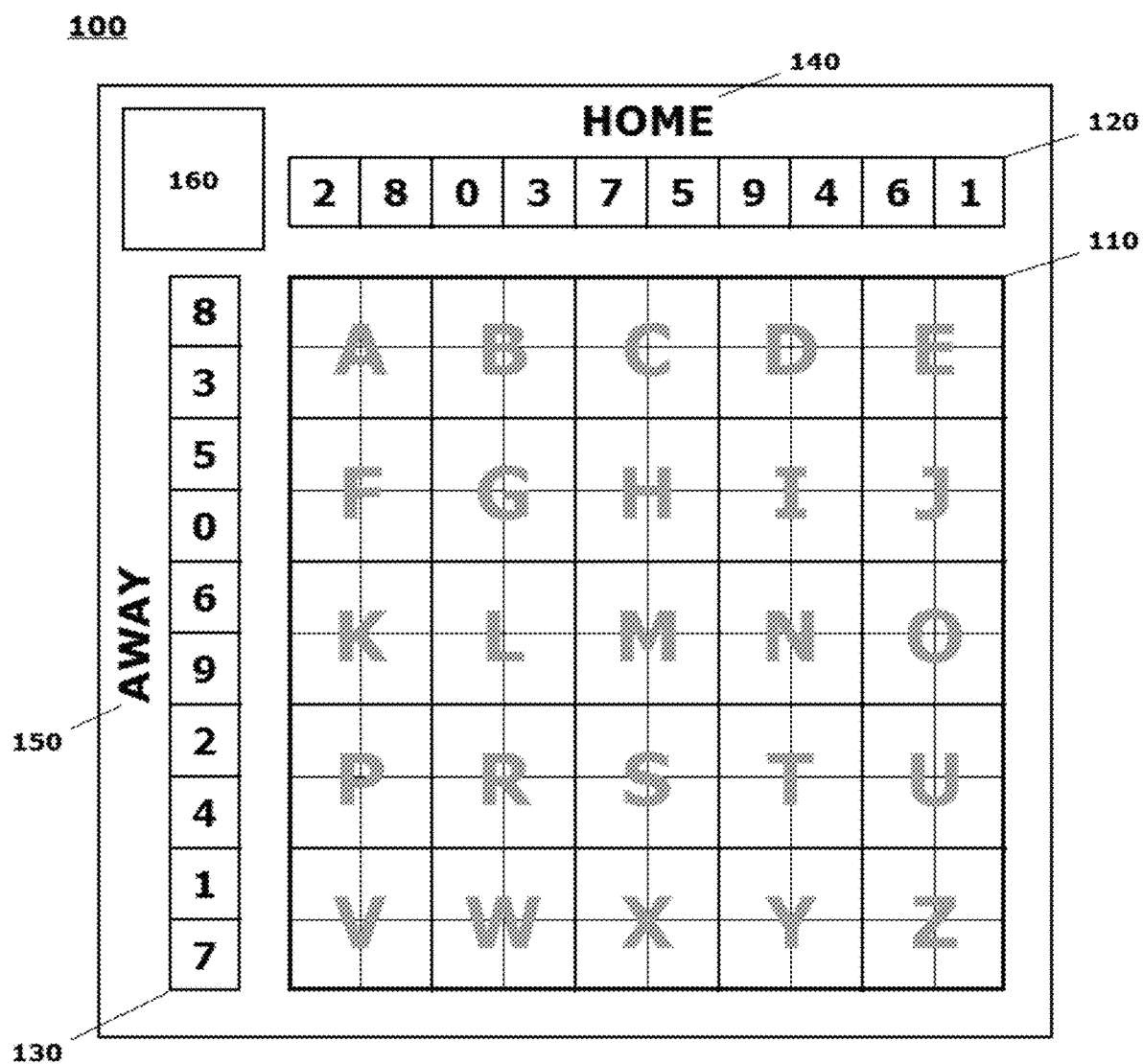
FIG. 1 schematically illustrates a typical embodiment of a Squares Game matrix form that may be automated according the disclosed schemes.

The systems and methods for uniquely adapting an automated and otherwise gamified Squares Game, which may be hosted on mobile and personal communicating and computing devices, to implement hybrid methods and systems employed by one or more of the myriad "fantasy sports" leagues that have become attractive to mass audiences across many sporting events and sports types, according to this disclosure will generally refer to this specific utility for those systems and methods. Exemplary embodiments described and depicted in this disclosure should not be interpreted as being specifically limited to any particular physical configuration of a user mobile computing or communicating device, or to any particular class of or protocol for, networked communication among devices of participating users. In fact, the disclosed systems and methods are not necessarily even restricted to user mobile devices. An electronic display component, which may display, for example, a matrix such as that shown in FIG. 1 may be usable to implement the disclosed schemes. Such display screens may include those associated with, for example, an Internet-based implementation accessed through a host website.

It should be recognized that any advantageous use of the systems and methods for gamifying a Squares Game and for providing the gamified Squares Games to a broad cross-section of a user population, in a manner that not only promotes participation in the games, but also provides for information exchange pursuant to immersion of a user in a reactive advertising scheme or environment that may benefit from processes, techniques or schemes such as those discussed in detail in this disclosure is contemplated as being included within the scope of the disclosed exemplary systems and methods.

The systems and methods according to this disclosure will be described as being particularly adaptable to enhancing a gamification experience related to randomized participation in a Squares Game related to one or more sporting events, and adaptations of such gamification as may incorporate certain features that have emerged as being particularly attractive in the context of fantasy sports leagues, and fantasy sports gaming. In embodiments, the disclosed systems and methods may have the advantage of collecting demographic (and even personal) information regarding participants in a manner that provides advertising, marketing and/or sponsoring entities with a body of analyzable data regarding those participants in order to target advertising content, including reactive advertising content, at those participants. In this regard, an amount of Business Intelligence regarding a participant population may be collected and made available, or otherwise provided for use, to interested parties and participating entities. Specific references to gamification and information exchange schemes are meant to be illustrative only in providing examples of real-world utility for the disclosed systems and methods, and should not be considered as limiting the disclosed systems and methods to any particular product or combination of devices, or to any particular type of electronically or physically sharable data vehicle. In other words, any commonly-known user personal electronic, computing, communicating and/or data display component, whether substantially fixed, or easily mobile, and including myriad emerging wearable technologies, may be incorporated into the overall scheme for automated gamification of the Squares Game.

In addition to the above-noted shortfalls in conventional Squares Games, those that have participated will readily recognize that certain score combinations (such as, for example, 2, 2 or 5, 2 in football games) are extremely infrequent winners of Squares Games. Historically, quarters and entire games of football infrequently end in scores that reflect these score combinations. Therefore, in traditional Square Games, holders of unfavorable score combinations receive little of the additional entertainment value, from the very beginning. The disclosed schemes may incorporate certain weighting or in process randomization schemes to be applied once the random numbers are chosen to better "level the playing field" in a manner that enhances participation for all participants even in the context of a single sporting event. For example, according to a pre-determined and pre-briefed schemes, periodically throughout the sporting event with which the Squares Game is associated, random number combinations may be shuffled, or in embodiments, separately selected for the reward of additional "prizes."

The disclosed schemes are intended to take Squares Games, which are infrequently hosted outside of the Big Game (one of the most widely viewed sporting events in the world every year), or are otherwise infrequently hosted by recurring basis due to their manually cumbersome nature, and provide a level of automation that may foster broader adoption of Squares Games over the balance of football games, and indeed across a more significant cross-section of other professional sports. A capacity of the disclosed schemes to reach a broader participating population may render the schemes more popular in their ability to attract many people without being tied, for example, to the restrictions of a closed viewing area among a controlled group in which a conventional host can most easily manually conduct, manage, play and/or oversee the Squares Game.

As will be described in greater detail below, the variability of the structure of the game application, including in-event re-randomization of the matrix may promote higher levels of participation, and continued interest for particular participants during an entirety of the sporting event with which the squares game is associated.

The disclosed schemes may prove particularly advantageous for many popular places where groups of fans congregate and consume sports (and food and beverages—potential advertisers for Squares Games), but which traditionally do not lend themselves easily to implementation of a manually-implemented Squares Game, because the participating environment is not necessarily lend itself to adequate oversight of the game play. Additionally, the disclosed schemes may prove particularly beneficial as additional incentives or "perks" at professional and collegiate sports venues in addition to sports bars, and, virtually any venue that may attract large viewing, including television viewing, audiences. In implementations, it is conceivable that tens of thousands of fans may enjoy participating in a plurality of individual device-implemented Squares Game.

In this regard, viewership and participation may be beneficially increased as individuals may be naturally inclined and interested to play.

The disclosed schemes, therefore, may provide an easy and controlled manner by which to educate, aggregate and enable large numbers of simultaneous players, even on multiple Squares Games among a particular group of participants. In this regard, the disclosed schemes are intended to render the traditional Squares Games, and innovations thereof, substantially more ubiquitous. In this regard, for example, it is not inconceivable that a million or more participants, for example, may be able to simultaneously participate in a single aggregated game related to a particular sporting event, or set of sporting events, with prizes and awards being allocated according to a predetermined scheme that makes a Grand Prize very attractive to the participating population, and yet is capable of rewarding different levels of awards and prizes to a broad spectrum of participants according to a scheme of participation that includes several levels of, for example, "tiebreakers."

In embodiments, variations on the conventional scheme are proposed that provide an increasingly robust, sophisticated and engaging employment of a basic automated. Super Squares technology. Among other objectives, these increasingly sophisticated schemes may serve to increase the likelihood of mass adoption of the Super Squares methods and systems, and adaptations to myriad associated real-world spotting events by implementing hybrid methods and systems adapted from the types of interactions that have emerged for use by fantasy sports leagues, which are becoming increasingly attractive to tens of millions of participants.

Further objectives of the disclosed schemes include providing elevated branding to certain entities in the form of marketers, advertisers and like forms of traditional sponsors that may desire to become involved locally, regionally or nationally in one or more Super Squares events, leagues, seasons or the like, in a manner that the "sponsors'" retail and/or website properties experience increased traffic (and therefore sales and exposure). It is anticipated that brands may be willing to subsidize or increase marketing spend for participation in one or more Super Squares schemes with an advantage of increasing funding for prizing, which can in turn increase users (and revenues) to the host and related parties.

The disclosed schemes may implement the popular Squares Game to achieve the above objectives. Embodiments may provide an automated opportunity to invite participation in simultaneous Squares Games associated with one or more sporting events, which also may be occurring actually or nearly simultaneously. Embodiments separately may provide an opportunity for a particular group to all participate in a same Squares Game in a manner that maintains the familiarity of playing the game among a group of friends, associates, colleagues, co-workers or the like. The disclosed schemes may provide the additional advantage that on occasions where the number of participants in a particular group is not enough to "fill" a particular matrix, other participants may be "allowed" into the particular game to maintain the fidelity of the game, the odds of any individual winning and the prize pool at requisite levels.

Based on the automated nature of the disclosed embodiments, these schemes may have particular other advantages over manual implementations in that, in embodiments, score combinations may be changeable among specified game periods within the Squares Game in a manner that provides heightened excitement to all, by enabling participants to avoid being left with unattractive score combinations for an entire duration of a particular sporting event.

In other variations, limitations that may be associated with traditional Squares Games can be substantially eliminated through automation according to the disclosed schemes.

In embodiments, for example, an event-long score tabulation and/or some manner of "Leaderboard Overlay" may be provided. Conventional Squares Games may provide an opportunity for what could be considered "games within a game." Generally, each "round" (typically tied to a particularly measurable duration or occurrence within the associated lives sporting event) provides a chance to win a prize, and each new round (new quarter, new inning, new period and the like) is its own self-contained event. Player participants without a matching score, according to the conventional scheme, essentially win nothing. In embodiments according to the disclosed schemes, it is possible to make user participation more attractive by modeling the Squares Game experience to mirror certain differing (and apparently successful) elements of "Fantasy Football" gaming. In embodiments, a leaderboard and/or scoreboard may be provided to reflect an ongoing (protracted or multiple-event) competition, or tournament-type, scheme between individual player participants, groups of player participants, or a virtual national audience.

The disclosed schemes provide a capacity to track and tabulate large volumes of player participant data in order that, for example, a tournament-type competition may be automated in a manner that would allow it to transpire across a full length of a sporting event broadcast (even involving certain specified events that may or may not occur in a pre-game and/or post-game section of a broadcast (televised) event, or a live venue event). In embodiments, scores may be tabulated and updated for each "round," and leaderboards may be provided to player participants on their mobile devices to allow those player participants to determine and track their individual overall standings against an entire population of player participants "competing" at any given time.

The disclosed schemes provide flexibility to determine and assign player participants to participation against subsets of an entire population of player participants as well. In embodiments, a particular leaderboard may be established, for example, to serve and/or support a localized (private or public) tournament involving some subset of all player participants. In this manner, "private" leagues, or even friends who are hosting a Big Game party, or associated with some other viewing type event, may be specified. Regardless, however, advertising content associated with the event, the host, a sponsoring entity, or the like may be provided in order that a prize pool may reach beyond the contributions of a small number of player participants. In embodiments, a series of local leaderboards representing sub-groups within a section of a stadium, sports bar, sports book or other participant-gathering venue may be specified.

In embodiments, a "national" or "global" leaderboard may be derived from an aggregate of some plurality, including all, local groups associated with a particular event may be implemented. Such a broad-based leaderboard may provide all users with standings as to how their individual results compare to all other player participants, in the aggregate. Such a national leaderboard may aggregate a large enough population of player participants, and/or may be more attractively sponsor-entity funded and supported, in a manner that supports the awarding of comparatively larger numbers of more significant prizes, when compared with local groups that may in include only enough participation to support the award smaller prizes, or merely to provide individual ones of the player participants with local bragging rights. Additionally, or separately, winning a local leaderboard may also provide a local winner an opportunity to access to another (broader) prize pool. In embodiments, a player participant designated as a local winner may be afforded an opportunity to participate in some manner of playoff or tie-breaker round, may gain access to other "selected" tournaments/events, may be entered in a separate "super" or "grand" price drawing, or otherwise may be awarded additional "perks."

In embodiments, for example, an event-long tournament and leaderboard may take a form of awarding points for various achievements, or levels of achievement, accomplished by player participants in each round, or according to any specified periodicity, accruing these points, for example, over a course of a sporting event, and displaying the accrued points via one or more separate leaderboard displays. A player participant may, for example, accrue points (or other markers, prizes, credits, or devices that can be collected and measured) for correctly responding to or answering reactive queries or questions. Such questions may include inquiries regarding some detail of product placement within an event broadcast, advertising content presented in an advertising insert provided on the player participant's display (including according to an implementing application), advertising content presented in an advertising provided in a broadcast or televised game's ad pods, advertising content physically provided within a sponsoring entity's retail location, or in online, print, email, social media post, or other mass media advertising, a product packaging, or advertising or event content displayed on, for example, a Jumbotron® (or similar display situated in public view at a live sporting event venue). In order to accommodate limitations common to live venues, such as, for example, crowd noise that may diminish a player participants' ability to hear sounds emanating from mobile devices and limitations to cellular carrier or wireless signal service in a venue, varying combinations of content display via mobile device to supplement public displays within the venue, and game element deployment via a combination of reliable SMS text messaging for query response selections, and bandwidth-dependent mobile applications for registration and leaderboard presentation may be deployed. It should be recognized that this example encompasses but one combination of such connected and complementary services that may make the Squares Game or Super Squares Game information available to each player participant in a manner that is intended to make the gaming experience enjoyable and comparatively "hassle-free."

According to the disclosed leaderboard schemes, for example, points may also, or otherwise, be awarded for correctly prognosticating an occurrence of a particular event in the game. Consider, for example, that points may be awarded for correctly predicting a pass or run, score, attendance, etc., or correctly recalling a portion of the preceding televised (or live, attended) game broadcast content. In embodiments, points may also, or alternatively, be awarded for a player participant opting into, or accepting, an offer presented by one or more of the game sponsor, a game host, a broadcasting network (including a TV network) or other involved entity. In embodiments such "opting in" may require participation of the player participant in a poll or survey presented by one or more of the above-listed entities. In such circumstances, point values may be assigned that are on par with point values that are associated with other activities of the player participant, or the different from the point values associated with the other activities. The assignment of such a point values may be at the discretion of one or more of the above-listed entities. In embodiments, the manner in which a particular player participant replies to any of the above stimuli may be afforded some "weighting" factor. Such an option may be considered one an offering determines that a benefit of weighting a particular manner of response does not serve, for example, as a disincentive to other player participants. Returning to the concept of the basics Squares Game, the automation of the game according to this disclosed schemes even allows for points, in the leaderboard format, to be awarded for securing a game square that is partially correct at the end of a prescribed game. An example of this would be where, a selected game square matches only the home or away team score, but not both. As an example, an individual player participant secures the game square 7/7. At the end of the quarter, the scores for the respective teams and in 7 and 3. The individual player participant may be awarded, for example, 3 points for the partial match, whereas a perfect match (home and away scores) might offer the same or more points (such as 7 points). Such a hierarchy of awards is analogous to betting on horse races in which the quinella pays less than the exacta.

In embodiments, player participants may earn certain applied score multipliers. One manner by which such score multipliers may be earned may be based on a particular player participant accomplishing one or more of (1) perfectly matching all score combinations (potentially across a variety of individually-secured squares) for each specified round, and (2) perfectly answering all presented questions. In embodiments, score multipliers may not require perfectly matching scores for all periods or questions, but may be awarded for each sequentially-consecutive pair or set of successful actions. In embodiments, an aggregation of score multiplier points may be accumulated according to match scores and/or matched answers, and a score multiplier may be applied for each of the player participants whose accumulated score multiplier points exceeds a pre-determined threshold. Score multipliers may be applied at the end of the game, multiplying the aggregate of all points accrued times a multiplier to determine a player participant's ultimate final score for the game. In a league-type or season-long scheme, score multipliers or "league" (or "seasonal") score multipliers may be accumulated and applied for perfect score matches, perfect matching squares, consecutive round matches and the like over multiple live participation events. A notification scheme may be provided to advise player participants, at specified or random intervals, where a particular player participant's score stands among other player participants in the league-type or season long play. It should be noted that, in differing embodiments, score multipliers may be applied inclusive or exquisite above any tiebreakers.

In embodiments, the particular player participant's "score," score multiplier or any tiebreaker may include, or otherwise take a form of, achieving a series of individual characters, which may be in the form of alphanumerics, emoticons, QR codes, images and the like, as well as combinations thereof. Consider an example that in a first round of a particular Squares Game an individual player participant activity is presented indicating that a correct response (or even any response) will result in the award of an "S." In a next round, a different individual player participant activity may be presented the completion, or successful completion, of which results in the award of a "C." Over the course of the several rounds of the event, the individual player participant may have to collect the letters S-C-O-R-E, a team logo and a "smiley face" (see :-)) emoticon. Only upon achieving this combination of in-event awards may the player participant then receive an overall event award, receive an event score multiplier, or other reward. In embodiments, it is easy to see how the words "SCORE" may be replaced with an identifier associated with the sponsor, the team logo may be replaced with a sponsoring entity's logo and the like. The ability to use these Super Square in-event award identifiers to spell words and brands provides myriad opportunities to overlay sponsorship promotions. It is even possible to allow player participants to select ALL Super Squares in advance of the start of an event, provided the selections spell a word, or brand, or some other restriction that provides player participants with the ability to pre-select their entries, but restricts the ability to necessarily select the Super Squares with the most favorable score combinations.

Using technology to access user registration demography, simulated virtual "tournaments" could be created, pitting subsets of users (e.g., according to any selectable demographic identifier, any region, a particular team affiliation, a particular brand association and the like). In this manner, a host of a tournament may be provided additional granularity as to the overall, or regional, demographics of the player participants in order to, for example, determine insights into how subsets of an overall player participant population may be faring with relation to one another. Such insight may be assist in providing appropriate feedback to, for example, sponsoring entities and better targeting their individually-sponsored activities for the player participants to a particular subset of the player participant population.

Virtual league or tournament leaderboards may be system created according to a particular user entity's requirements. In this manner, information about the population of player participants, and identifiable sub-groups within that player participant population may be tracked according to known BI and/or CI methods. Information reportable from the system according to player participant population demographics may be sanitized of all particular individual player participant identifying information including, but not limited to, user names and other player-participant provided identification information that should be kept confidential and/or limited according to any participation agreement between, for example, a game host and individual player participants taking part in the particular game. In embodiments, any display of player participant scores, and the like, for comparison would not need to, and therefore would not provide player participant identities. Multiple group subsets, or sub-groups, could be displayed (e.g., results of fans of all teams in a sports league, cities of a state, largest cities in the country, or according to any other like "indicator") The use of these virtual tournaments (and reporting on same to the mass audience, via app, broadcast, other media, or some combination of some or all) may be considered to provide interesting content to some or all of the audiences. As mentioned above, such virtual demographic leaderboards may provide the Super Square event host with an ability to target sponsoring entities in order to sell sponsorship rights in events associated with these virtual tournaments and leaderboards.

The disclosed embodiments introduce technology to provide a practical manner by which to handle the distribution of Squares Game matrices, as well as providing a flexible process of selecting and assigning the squares, along with aiding to collect any entry fees, tracking the results, and distributing the prizes. In embodiments, a robust computing backend is provided to track large-scale populations of player participants and to provide the computing overhead to manage differing game constructs, subsets of player participant populations, and awards/reward schemes as are discussed in varying detail throughout this disclosure.

While the disclosed embodiments may incorporate components that apply to (and be substantially based on) traditional ten by ten matrix games, it is anticipated that popular implementations may be found in the five by five matrix version denoted by the darker lines and the letter annotations shown in the matrix participation area 110 in FIG. 1. Such an implementation may be discussed below as a "Super Squares" variant of the game.

"Pre-game" or pre-event Squares Game matrices may be provided in centralized locations, perhaps with URL's, unique letter designations, or QR codes inside of each square, which could allow player participants to enter a particular square's URL or unique letter into a web address or window of a supporting website or mobile application, or, for a player participant to select a square by scanning a square-unique QR code (on a displayed Squares Game matrix), or click the square on a display, which would allow the player participant to select that particular square.

In embodiments, the disclosed process, as enabled by hosting Squares Games electronic devices, may provide formatting options. For example, instead of randomly filling out the ten column and row "score heading" sections with random number from 0-9, the score heading(s) could be fixed, and the internal 25 or 100 matrix squares could instead be "jumbled" once the entry phase of the game is closed, and selections of squares are final. Such a manifestation of the traditional Squares Game would be virtually impossible to accomplish in a conventional paper environment, but is relatively easily implementable in a virtual electronic-display environment.

According to the disclosed schemes, Super Squares Games may provide a method by which a mass audience can participate in Squares Games, hosted by a network, sports venue, team, advertiser, individual, ad sponsor, event sponsor or the like. While traditional "sales" of squares may be enabled, it should be recognized that other "prize" schemes are implementable and may be preferable in certain jurisdictions and/or scenarios. Due, for example, to the perceived degree or impact of luck (chance) required to win a game, and what is anticipated to become a very public nature of the game, it may be advisable, or even required in certain jurisdictions, to avoid charging for participating, and instead to offer other incentives (rewards) for participation, including entries (squares) in exchange for participating in reactive or ad-supported versions of the game. The addition of skillful queries and questions, particularly as a final determining step of qualifying winners, may also be required in certain jurisdictions and according to applicable laws. Entry into the game itself may be controllable via a particular set of conditions established by any of the above-listed hosting-type entities.

When participating in Super Squares Games, jumbo 4×4 squares are selected by player participants, five across horizontally and five up and down vertically (5×5), meaning that there are only 25 "Super Squares" to choose from, each representing 4 number combinations (4 times the number of score combos for participants, and 4 times fewer squares to sell/fill). Each Super Square can be lettered A-Y (25 letters) or A-Z (with one letter of 26, from A to Z, being deleted), or representing a choice that essentially asks that the matrix square be randomized. Using letters makes it simple to select and record a square choice, and to share a particular player participant's square(s) choice with others as opposed to using the X and Y axis matrix address. In embodiments, a game or event host could remove the "I" or "Q," (the latter being shown in FIG. 1), to avoid the visual confusion of I with a number, or the letter "Q" with "0." Separately, the letter Q, in embodiments, may be sued to select a randomized "Quick Pick" of a Super Square. In such a Quick Pick digital environment, those that select "Q" could be randomly assigned a letter, either before or after other interior squares are completed and/or jumbled.

A limitation of mobile phones is that a ten by ten annotated grid may be difficult to display and even more difficult to manipulate correctly on a small screen. If presented on a television or other larger format display screen, QR codes may be placed in each square. It is recognized that, in mobile screen applications, the QR codes could be too small or close together to be easily scanned without inadvertently scanning the wrong QR code. Therefore, a less error-prone method of allowing a user to select an interior square may be to refer to each square by a letter. A host could therefore utilize a lettering system to select a square ("Enter your letter HERE: _____") as opposed to requiring the participant to press a section of a screen or scan a too-small QR code, thus providing an entry option that may eliminate some complexity and errors that are more likely in such examples. Another method of visual presentation may include skewing the squares matrix at a 45 degree angle, such that the score identifiers appear along any adjoining edges of a now diamond-shaped matrix. This visual presentation may be more ideally suited for displays that are viewed in a typical "landscape" mode, such as television displays, where the viewing area ratio is 4:3, or more commonly, 16:9 (width to height).

Because the digital display of the matrix is easily changeable, and as mentioned, a particular scheme can be implemented randomly to attempt to avoid a frequency with which participants obtain unfavorable scores, or, for example, scores may be re-assigned between rounds. Separately, Super Squares Games can offer clusters of score headings that can implement the scheme by which to attempt to ensure that at least 1 of the 4 Super Squares score combinations is statistically more favorable than average. Also, the rules of the Super Squares Game may require that either the interior Super Squares are jumbled once more each round, or, to ensure more variations, the audience of participants can select a new letter each round, which is then jumbled.

Each sport can manipulate score headings that statistically increase a likelihood of securing at least one favorable combination of the four encapsulated by the participant's Super Square. By way of example, each cluster of score headings could include a high frequency occurring score, and a lower frequency occurring score, based on statistical averages. Note, too, that as Super Squares Games associated contests may be broken into discernible rounds with three to six rounds potentially being specified per contest or live event. As scores tend to increase with time, in early rounds, having lower digit score combinations may be considered to be more favorable, where higher digit score combinations may be more valuable in later rounds (near the end of the underlying contest or sporting event, for example). This is particularly true of comparatively low scoring games like soccer, hockey and baseball (to an extent).

In embodiments, the score headings and assigned letter allocations may be permanently displayed, and a participant may be assigned a random letter (and therefore, the Super Square and its related score combinations). This provides a consistent and simple means by which to quickly illustrate and distribute Super Squares, without the need to illustrate the "jumbling" process of score headings or squares. This may distribute at least one favorable interior square per Super Square.

As an example, a recipient of a Hockey Super Square "M," may always receive the Home/Away score combinations of 2/2, 2/7, 7/2, and 7/7. Participants could therefore eventually become familiar with the score combinations linked to each letter.

The disclosed Squares Games and Super Squares Games may be sponsored by advertisers to (1) defray, avoid or supplement the cost of entry distribution, (2) advance logistics of hosting, registration, winner selection and participant notification, and/or (3) provide alternatives to monetary prize pools for non-monetary Squares Game and Super Squares Game implementations. Squares Game and Super Squares Game sponsors may provide advertising content that may be randomly interspersed with displays of the prize matrix at the sporting venue, or within a broadcast of the game. The advertisements may be made reactive in a manner that may be described for example in U.S. Pat. No. 6,606,745, the disclosure of which is hereby incorporated by reference herein in its entirety. Correctly responding to reactive queries may result in heightened attention (something every advertiser desires) and additional rewards to Squares Game and Super Squares Game player participants.

Particularly for large mass audiences (such as televised programs) where millions of viewers (and potentially player participants) may be viewing, the heightened attention paid to ads that are associated with the Squares Game and/or Super Squares Game (denoted with an alert, mark or tone) may increase the value of an sponsor's advertisements, meriting a premium being paid by the sponsor. This premium may not only generate additional profits to the sponsor, sports league, broadcaster, post, or other participating entity but a portion of this premium might offset cost of conducting a mass Squares Game or Super Squares Game event. This cost might also include the cost of a significant prize (such as a car), or an insurance premium to cover the cost of offering massive grand prizes.

The public offer and promotion of the Squares Game or Super Squares Game, and the offer of more valuable prizes (new cars, or significant prize pools) might increase live venue attendance and increase broadcast viewership of the sporting event (and therefore the audience for the advertisements). An increase in viewership and attention paid to the advertisements (measurable through the reactive advertising concept) may increase a value of an advertisement inventory, further increasing the revenues generated from the advertisements. This increased revenue stream can be partially diverted back into prizing, creating a positive feedback "loop" that increases prizes, then audience size, then prizes, and so on.

In embodiments, attendees at live venues (or watching TV broadcasts) select a Super Square letter 4-6 times or more over the course of the event, and watch a reactive ad before each "shuffle," to qualify for a Super Square, if answered correctly. Failing to get the reactive question correct might result in the attendee not being registered as a player participant for that round, or the player participant only retaining one of the four squares (perhaps the least desirable one in the combo).

The disclosed schemes for implementing a Squares Game or a Super Squares Game may be paired with skill-based and prognostication elements to allow for sponsors to charge to play the games, or, they can be entirely subsidized by the venue, sponsors, or broadcast networks. The skill-based or prognostication questions might add yet another a tiebreaker element. In embodiments, a "Jackpot Shot" question could ask, "What will be tonight's attendance," or "How many shots on goal will be made this evening?" This differentiator could be used as a "closest to the correct answer" tiebreaker, or may be required to match the result precisely to win a particularly valuable ("super") prize. Smaller prizes can be awarded each period/quarter/increment, with a super prize being awarded to a player who wins all 4-6 periods, and, optionally, the Jackpot Shot.

As part of participating digitally, a player participant at a venue may be required to provide their seat number and name when registering, allowing the host to contact participants (and to film them using onsite cameras), integrating the Squares Game or Super Squares Game into the live event as an added attraction. Similarly, on-air hosts might have real time access to the player participants and their ongoing entries, allowing them to be called or contacted on-air during the corresponding sporting event. This variation provides a real time, social media-friendly component to sporting events, which may be attractive to certain demographics.

In embodiments, as is mentioned above, a particular means of increasing interest and participation from all involved may be generally provided in increasing prize levels, which may be funded by sponsors particularly desiring greater direct connectivity with an entire population of player participants, or a particular sub-group of the overall player participant population. According to the methods described above, all manner of deployment of additional branded integration may be provided from branded backgrounds for participation screens, to particular logos randomly placed or "popping up" on participation screens, to identification of prizes being provided according to particular branding. In embodiments, player participants may need to visit a particular sponsors website and/or physical location in order to redeem or collect particular awards/rewards. According to these schemes, player participants may have access to larger Squares Game or Super Squares Game prizes pools, for themselves and also potentially for invited friends, by engaging in a particular activity by which an individual player participant may verify a visit to a sponsoring entity's physical and/or online properties. In a manner similar to the schemes described above for achieving an applying a scores multiplier, specific actions of individual player participants may elevate the standing of the individual player participants to, for example, a "Super Player," permanently, or for the duration of a tournament, season, day, league, or individual event. Again here, player participant actions may include the scanning of a QR code, or the physical entry of a code into the Squares Game- or Super Squares Game-enabled application, or the downloading of the sponsor's gaming or other application at a retail location, from an app store, or via a code or instructions provided on sponsor's website. This Super Player status may drive site and foot traffic in advance of the game, and also turn the physical or online properties into promotional locations. Sponsors' physical or online properties may even offer ability to upload the Squares Game- or Super Squares Game application in a native version, or in a special version of the sponsor's own application Squares Game gamification capability enabled. In embodiments, other related schemes may allow users to obtain a game clue, game points, or other items that would provide an advantage in a coming Squares Game or Super Squares game event, tournament, league, or season.

Additional variations on this theme may be implemented. For example, a Super Player who wins a Local Group or National Group event may also lead to others in the Group (Super Players or standard player participants) to receive prizes that would not have otherwise been won by the standard player participants, but which are unlocked in their use based on their relationship to the designated Super Player, and the benefits bestowed through the sponsor, to "friends," leaderboard group members, or others somehow "linked" to the winning or designated Super Player. Super Players may receive special icon designations, which may appear next to their identifiers displayed leaderboards, and other displays. This adds to interest in the sponsor, and due to the increased benefits (including an increased or separate prize pool or rewards available to Super Players), individual player participants without the Super Player icon may be invited, urged, or otherwise asked to visit the sponsor to become, or as a step in becoming Super Players themselves. In this manner, it is envisioned that peers will influence friends to take the necessary steps to "upgrade" to Super Player status as additional individual player participants acquiring such status may inure to the benefit everyone in a particular player participant group, or overall. In embodiments, information regarding Super Players, and the sponsor, may be provided to event hosts, sporting event venues, broadcast networks and the like in order that some recognition may be further provided to the status of participating individuals as Super Players in the Squares Games or Super Squares Games associated with the event or broadcast. Such positive references may provide tangible promotional value to the sponsor, as well as elevating the positive commercial bond between event attendees, individual player participants, Super Players and the brand and brand sponsor.

Once a leaderboard model according to the above-described scheme is adopted by a Squares Game or Super Squares Game host, and a number of player participants, has been established, the disclosed schemes may provide a capacity for ongoing daily, weekly or season-long leagues and tournaments to be supported. In embodiments, a reviewable "standings" board may be displayable on individual mobile device screens or on display screens in public venues for displaying current standings in the league, season or tournament play of the public or private leagues. Groups of player participants may might create their own Squares Game for Super Squares Game leagues, or have periodic games (daily or weekly), which may even be defined across multiple sports disciplines. In embodiments, certain head-to-head competitions may be specified so as to generate "wins" and "losses" for each team, group of individual player participants, or individual player participants themselves during the season. Where permitted, a capacity to implement a scheme for wagering may be provided. The disclosed schemes may enable a host to charge player participants for the opportunity to play, and, in addition to advertising revenues, can supplement the prize pool(s) with such entry fees. In embodiments, the prizes may incorporate Super Player prize premiums substantially in the manner described above, with paying and non-paying player participants, to provide different leagues based on prizing, or different prizes within one league based on the status of the designated winners.

In some professional and college sports leagues in the United States, multiple broadcast network feeds of games are provided to a national audience. Often, these broadcasts are ranked-ordered such that games most relevant to local markets are prioritized. For example, many professional football games commence at 1:00 PM EST Sunday, and again at 4:15 PM EST. Each feed may serve only one or several football games to any distinct market, so that the aggregated number of viewers, nationally, is significantly greater than in any one market. For example, a small market game between less followed teams may only draw 1.2 million viewers in two markets during the 1:00 PM EST slot, but the other 8 feeds, in aggregate, may attract 16 million viewers. Under this scenario, local groups may allow player participants to compete in real time within a local league, with the requirement that each player participant selects a local feed broadcast. Still, however, the player participant may be able to separately participate in a Squares Game teams in a non-local market, with both games being broadcast at approximately the same time. As it is unlikely that round terminations will be synchronized, the system may provide timing synchronization across the games in order to allow each player participant to respond during their own defined "Check-In" period, with a group or national leaderboard not being shared with all users until after the last game and feed has reached a round completion or termination point.

In the above described manner, a Squares Game or Super Squares Game host may automatically aggregate all games into one or more national, regional or sectional leaderboards, increasing the available prize pool by aggregating varied revenue streams from multiple markets with regard to sponsorship (on a local, regional or national scale), ad and product placement (on a similar local, regional or national scale, Super Player premiums, and individual player participant entry fees, where unauthorized and appropriate). Aggregated prize pools may attract more viewers, who in turn may become additional Squares Game or Super Squares Game player participants across multiple markets, cumulatively, having an effect of increasing advertising revenues and concomitant prize levels. In embodiments, similar aggregation may occur across multiple live events in a same day. For example, player participants may participate in the 1:00 game and the 4:15 game, and may be provided an option to "cash out" after the 1:00 game, or to "let it ride" through the 4:15 game, and even through the 8:00 game, or even through a Monday game as a tiebreaker. Daily grand prizes and jackpots might be awarded to users with the highest score when aggregated across all games in a defined period. In embodiments, aggregated "scores" may even be collected from multiple sports over a defined period, particularly when sport seasons overlap (such as when there are hockey, football, and basketball games occurring within the same day or week).

Each March, potential player participants gather to individually complete their brackets prior to the commencement of a 64+ team tournament. Potential player participants predict the outcome of each matchup, over a series of predicted pairings reducing the field progressively to 32, 16, 8, 4, 2 and 1 overall winner, over 6 rounds and several weeks. A reasonable estimate for a single player participant to predict correctly all game outcomes in advance of the tournament, a feat which has never been reported to date is 1 in more than 100 billion.

Embodiments according to the disclosed schemes may adapt a Squares Game to the prognostication thrill of bracket selections in advance. The quizzing, prognostication, and rewarding matching score elements of the Squares Game or Super Squares Game may be adapted to allow individual player participants for each bracket round (e.g., the opening round of 32 games) an opportunity to select one game and predict the outcome of the game (winner, and optionally, tiebreakers as discussed below). In embodiments, the disclosed schemes may afford an individual player participant an opportunity to select multiple games over certain periods such as, for example, an early Saturday game and a late Saturday game. The Squares Game host may enable a Squares Game in which a new square is allocated each round within a particular game, or to remain constant for the duration of the game. Player participants may be afforded an opportunity to select the squares. In embodiments, individual player participants may be required to select a single game and winner for each round in advance of the commencement of the tournament, as opposed to selecting a winner of every game and subsequent round. In embodiments, individual player participants may be afforded an opportunity to select a new winner for each round, once the prior round results are concluded and a list of the remaining teams from which the player participant may select is established. This wider variation may mediate the risk to an individual player participant in attempting to select winners in later rounds for which the individual player participant may have already been eliminated. Given the capacity and adaptability of the Squares Game concept to variations in selection, scoring, cumulative scoring and prize awarding, the "bracket" version may include an automated implementation that permits individual player participants to select only among games of their choosing, selecting a winner, and also permitting individual player participants to select squares to coincide with a particular round, in a manner that may be pre-determined by the host, or by the individual player participant. By way of example, the automated scheme may provide for a capacity to collect information from individual player participants regarding a selection of a game of their choice, a prediction of the winner, and a selection of any square of their choosing for any round of their choosing. In embodiments, the automated scheme may otherwise require that the square be selected for the final round. This variation may permit a player participant to select a single square for each round, in advance.

Each of the variations of the automated Squares Game applied in a bracket context may afford player participants a considerable amount of control over their entries even as the tournament progresses. Individual player participants, for example, may associate squares with their individual selections and prognostications for specific games, winning teams, and squares relative to the final score, or for any round or rounds. This level of player participant interaction and control may provide a favorably perceived condition relative to the involvement of large groups of player participants, and may provide an advantage to player participants who pay closer attention to the actual progress of the games, teams, and players involved in the turn of allowing the individual player participants to exercise their knowledge when selecting games, outcomes, and squares and related score combinations, even as unexpected occurrences wise in the progress of the tournament.

An advantage of the "bracketology" Squares Games or Super Squares Games is that these schemes combine interplay with audiences attracted to both games while simplifying the qualification process, thereby providing ability to attract a wider audience.

The automation of the Squares Game in this adaptable format may also provide flexibility for a host to create and implement a rules structure prior to commencement of the tournament that effectively employs known or calculable statistical measurements of certain events occurring, in order that the likelihood of winning according to this scheme is significantly easier than selecting a perfect bracket according to the traditional method. Also, the use of aggregated Squares Game points and leaderboards provides all player participants, over the course of the tournament, with the ability to remain "in the game," even in the event that the individual player participant may have, at some point over the course of the tournament, fallen out of contention for the jackpot or mega jackpot prize pool.

It should be recognized that games according to the disclosed Squares Games or Super Squares Game gamification schemes may provide an automated platform for individual player participant interaction that is likely attract many millions of individual player participants over a widely viewed sporting event or tournament of games, it is possible that there may be multiple player participants with identical point scores, and even with "Perfect Super Square Matches" over a period of time (such as after four or six rounds of Super Squares). To avoid the use of a random drawing to break ties, pre-determined and/or pre-planned player participant-selectable tiebreaker tools may be automated. In embodiments, one category of such tiebreaker tools may incorporate a particular player participant skill set exemplified in the Squares Game or Super Squares Game. These may include prognostication, ad attentioning, and/or content attentioning.

In exemplary embodiments, one or more prognostication questions may be derived and presented to the individual player participants at some specified, or random, time prior to the event. Tiebreaker points may be awarded during the event then based on how close a player participant's responsive estimate comes to the actual correct answer. The number of maximum points (say, 3 points) would be awarded based on either a proximity to accuracy. By way of example, prior to a football game, each player participant may be asked to estimate a total number of yards to be gained by a particular running back. A maximum allowed variance may be set at, for example, 40 yards, plus or minus. If a particular player participant's prognostication misses the actual number of yards gained by the particular running back by 4 yards, the individual player participant will be deemed to have gotten the answer 90% correct. In such an instance, the individual player participant may be awarded 9 of 10 available tiebreaker points. The prognostication events, variations, and available points may be set by the host prior to the game via an administrative portal accessible only by the host to modify the point schemes for the Squares Game or Super Squares Game to which the football game is linked. The tiebreaker scheme may be applied over any number of over tiebreakers, and ultimately result in an aggregated resulting in a total tiebreaker score, which can be added to a total of a player participants accrued points, modified according to any multipliers, when appropriate and only to break ties in 2 or more player participants' aggregate scores to determine a single winner.

In embodiments, when an objective is to award only one grand prize to only one player participant, the tiebreaker scheme may be particularly rigorous. Variations and prognostications may be weighted, multiple part responses may be required (including answering one or more characteristic questions regarding the event, the broadcast, the event or the like) and/or a hierarchy of correct responses and/or prognostications may be established according to known methods to break ties. The system may provide unlimited, or only limited, opportunity for a host to locally or regionally modify the rules in any manner that affects awards/rewards. Important to the fidelity of the implementation of any Squares Game or Super Squares Game according to this disclosure will be in and ensuring that all player participants are advised and/or informed of the rules prior to the commencement of play. In this regard, the disclosed systems may provide standard sets of instructions and standard deviations from those instructions that individual player participants will be required to acknowledge prior to commencing a particular game, group of games, league and/or tournament.

The disclosed schemes may also provide matrix-based selections that are not "scores" based at all, or that do not require the provision of "scores-based" matrices, in multiple variations and schemes that may be optimized to particular sporting events.

A means of increasing the likelihood of winning for player participants could include requiring a number of winning Super Squares over the course of an event, eliminating the requirement that winning Super Squares be consecutive from the first round. By allowing the consecutive winning rounds to commence from the first, second or third round would increase the likelihood of a player participant winning (though it would make it impossible for the player participant to achieve 5 consecutive winning Super Squares, of 6 rounds, should they be authorized to commence from the third round).

The host could allow that the consecutive requirement be eliminated entirely; in such an example, the requirement may simply be, "Collect 4 or 5 winning Super Squares over the course of this event." Alternatively, the host could provide one or more "mulligans," or "do-overs" per event, such that, while the consecutive winning Super Square requirement may remain intact, a participant could receive, earn, or purchase a "mulligan" that could be electively utilized to convert a losing round into a winning round.

Another means of increasing the likelihood of winning would be to allow some or all player participants to select their own Super Square combination in advance of a round, such that player participants with a thorough knowledge of the game might have an increased likelihood of selecting a winning combination. This "Pick Your Square" bonus could be awarded randomly (such as to those who are awarded the letter "Q"), or could be otherwise received, earned or purchased. For example, in a low scoring game like hockey, where scores are often 0-0 after the first period, selecting the Super Square containing a "0-0" combination would provide an increase in the number of winning Super Squares in that round.

A host might also increase the likelihood of winning by further reducing the number of Super Squares. The host may elect, for example, to create only 5 Super Squares, in which a shape of each cluster of twenty combinations in a ten by ten matrix may deviate from a true "square" shape. The host might also add a "common zone" within the overall matrix that may be similar to the center square of a Bingo card, which is marked as filled for all player participants. The host may, for example, purposefully allocate frequent or infrequent scores to the shared zone to further impact the frequency of winning Super Square combinations.

In embodiments, the disclosed schemes may be adaptable to sporting events where numbers are frequently used, but for other than traditional scores. For example, in many racing events, there are no "scores," merely finishing outcomes/orders (first, second, or third.) Numbers, however, are worn by players or event participants (such as in professional motor sports, like auto racing, in which the numbers are displayed on the cars/trucks/motorcycles).

By way of comparison, the "score headings" may be replaced with "driver/car numbers" and "Home" and "Away" might be replaced with "First Place" and "Second Place," for the event where Super Squares may be awarded at lap intervals. In such an implementation, for a 300 mile race, there may be Super Squares awarded every 50 laps, totaling 6 intervals. By way of example, at the 50 lap mark, the first place car might bear the number "17," and the second place car might bear the number "3," meaning that the holder of the Super Square "7,3" would have a winning Super Square.

A racing-inspired Super Square game could have applications to other forms of racing, including motocross, horse racing, and dog racing, and separately to non-racing events like jai alai and other sports where numbered event participants are ranked based upon their finish.

Finally, for events where finishes are ranked numerically, but where the event participants are not numbered visually (i.e. golf tournaments), a host could assign a number to each event participant in advance of the event (as in a golf tournament, where upwards of 100 golfers compete). So, in such an example, the top finishing golfer was assigned #42, and the second place finisher is golfer #2, the Super Square participant holding the "2,2" Super Square over a certain interval (i.e. after the first round, or first 9 holes) would be a winner.

The disclosed embodiments are intended to represent non-limiting examples of variations to the Super Squares games implementing the disclosed schemes in many variations and encompassing "scores-based" games, and variations that are associated with "non-scores-based" games. All of the above are non-limiting examples of potential implementations. Further, the totality of the above discussion advises multiple variations on the traditional or conventional Squares Game in order to modify the game in a manner that is commensurate with a desired level of participation and/or modify the game in a manner that properly allocates awards/reward, and a potential for multiple winners, according to an available prize pool in consideration of the actual level of participation. Finally, the disclosed schemes are intended to advantageously integrate, in an automated manner, attractive attributes of the basic Squares Game, fantasy sports prognostication, availability of wagering (where authorized), and attractiveness in the marketplace not only to individual player participants but also to potential sponsoring entities.

Figure 2:
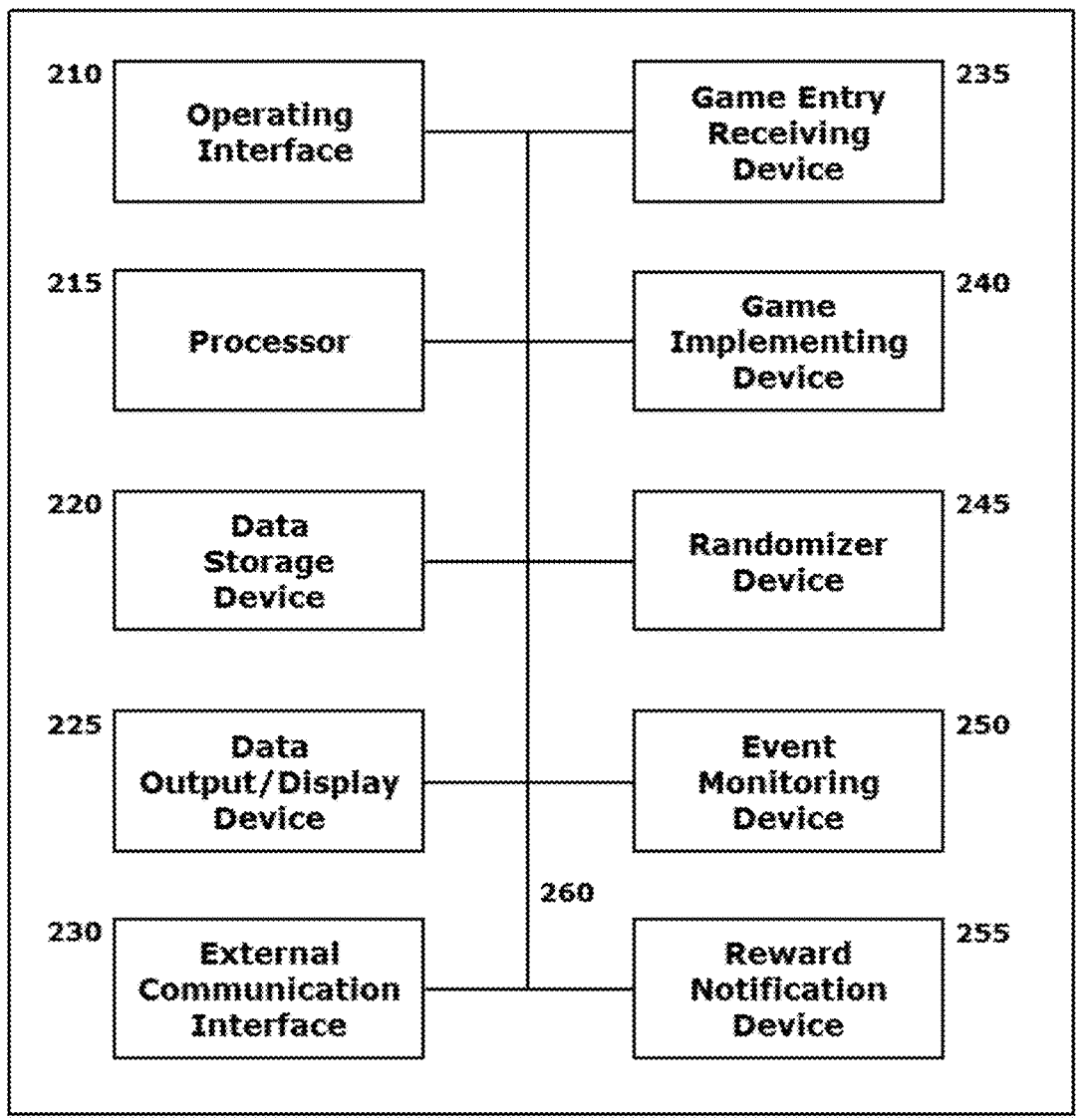
FIG. 2 illustrates a block diagram of an exemplary system for implementing an advanced automated Squares Games according to any of the varied schemes outlined in detail below in this disclosure.
Figure 2:
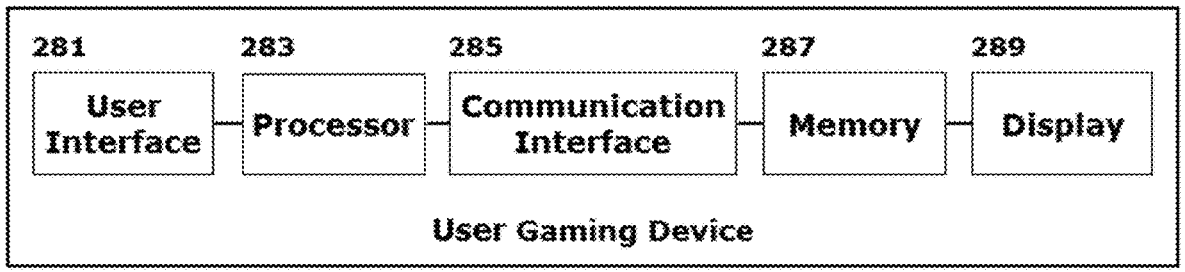

FIG. 2 illustrates a block diagram of an exemplary system 200 for implementing an automated Squares Games according to this disclosure.

The exemplary system 200 may include an operating interface 210 by which a user as a host may communicate with the exemplary system 200. The operating interface 210 may provide a host an opportunity to initiate the automated Squares Game and to input any parameters appropriate to the conduct of the automated Squares Game in the manner outlined above including parameters for aggregation of discrete Squares Games and establishment of tiebreakers, among other parameters that may be user-selectable by the host. The operating interface 210 may be configured as one or more conventional mechanisms common to computing and/or communication devices that may permit the host to input information to the exemplary system 200. The operating interface 210 may include, for example, a conventional keyboard, a touchscreen with "soft" buttons or with various components for use with a compatible stylus, a microphone by which the host may provide oral commands to the exemplary system 200 to be "translated" by a voice recognition program, or other like device, including any emerging wearable I/O device, by which a user may communicate specific operating instructions and pre-determined parameters setting to the exemplary system 200.

The exemplary system 200 may include one or more local processors 215 for individually operating the exemplary system 200 and for carrying into effect the disclosed schemes in the exemplary system 200. The processor 215 may carry out routines appropriate to operation of the exemplary system 200, and may undertake data manipulation and analysis functions appropriate to the implementation of the Squares Game in any and all of the above-noted variations including, but not limited to, aggregation and/or leaderboard tracking. Processor(s) 215 may include at least one conventional processor or microprocessor that interprets and executes instructions to direct specific functioning of the exemplary system 200, and control of the automated Squares Game implementation in any of the variations from a mirror of the conventional Squares Game, modified as a Super Squares Game, or otherwise varied to include aggregation, leaderboard tracking and/or tiebreakers according to this disclosure.

The exemplary system 200 may include one or more data storage devices 220. Such data storage device(s) 220 may be used to store data or operating programs to be used by the exemplary system 200, and specifically the processor(s) 215 in carrying into effect the various player participant interacting, game displaying, leaderboard tracking, aggregation, Super Player identification and all forms of rewards notification functions of the disclosed Squares Game and Supers Squares Game schemes according to this disclosure. At least one of the data storage device(s) 220 may be used to store the gamification application and to temporarily store in-process Squares Game matrix display information. At least one of the data storage device(s) 220 may be used to store particular identification information that may be collected incumbent to individual player participants requesting to play the game, or to register for particular league, tournament, season or selection of events. Such data storage device may also include cumulative scoring related to participation of each individual player participant according to any one of the implemented game if the case and scenarios. The data storage device(s) 220 may include a random access memory (RAM) or another type of dynamic storage device that is capable of storing updatable database information, and for separately storing instructions for execution of system operations by, for example, processor(s) 215. Data storage device(s) 220 may also include a read-only memory (ROM), which may include a conventional ROM device or another type of static storage device that stores static information and instructions for processor(s) 215. Further, the data storage device(s) 220 may be integral to the exemplary system 200, or may be provided external to, and in wired or wireless communication with, the exemplary system 200, including as cloud-based storage components.

The exemplary system 200 may include at least one data output/display device 225, which may be configured as one or more conventional mechanisms that output information to a user, in this case a host, on a progress of the Squares Game. The data output/display device 225 may be used to indicate to the host information regarding a compilation of the matrix for a particular game, as well as a progress of a live event with which the Squares Game is associated. It is not necessary that the host monitor the actual conduct of the automated Squares Game by the exemplary system 200, but the host is afforded that option. Further, the data output/display device 225 may be in the form of a printer or other data delivery means by which the "rules" of a particular game may be provided to each individual player participant, particularly as those "rules" may be modified by the host for a particular playing of the game.

The exemplary system 200 may include one or more separate external communication interfaces 230 by which the exemplary system 200 may communicate with one or more offboard Squares game implementing components including, but not limited to an external display, and any user gaming device 280 on which a participant may choose to play the game, which may be in wired or wireless communication with the exemplary system 200. It is anticipated that components of the exemplary system 200 may communicate with a broad spectrum of displays and user gaming devices 280 that may generally be employed by each player participant in execution and monitoring of his or her individual participation in the Squares Game, tournament, league, event or the like.

The exemplary system 200 may include a game entry receiving device 235 that may be used to receive and store individual player participant registration/identification information for individuals seeking to participate in a particular Squares Game. The prospective player participant may have to identify the live event to the exemplary system 200 with which the prospective player participant may choose the Squares Game to be associated. In addition to receiving prospective player participant registration/identification information, the game entry receiving device 235 may be usable to interact with the user's gaming device 280 to receive a user selection of one or more of the plurality of squares in the game matrix for the particular Squares Game in which the individual player participant intends to participate. Individual player participant selection of the one or more of the plurality of squares in the game matrix may be according to any of the above discussed methods, including all manner of automated means or user manipulation of a user interface associated with the individual player participant's user gaming device 280.

The exemplary system 200 may include a game implementing device 240 that may execute functions for carrying into effect the Squares Game according to the disclosed schemes, and as modified by the host, in the exemplary system 200. The game implementing device 240 may itself be a function of the processor 215, or may exist in the exemplary system 200 as a stand-alone component.

The game implementing device 240 may accept input from the game entry receiving device 235 and the randomizer device 245, which may generate the random number schemes described above, to generate and monitor the status of the game matrix throughout the duration of the live event with which the Squares Game implemented by the exemplary system 200 is associated.

The game implementing device 240 may also be usable to undertake the prescribed aggregation scheme across multiple games or across multiple events, and otherwise to implement and track the disclosed leaderboard scheme.

The exemplary system 200 may include an event monitoring device 250 that may be usable to monitor the progress of the live event with which the in-process Squares Game is associated. At prescribed intervals (rounds), the game implementing device 240 may receive inputs from the event monitoring device 250 regarding, for example, a score, or other progress, of the live event and begin a determination scheme by which to determine whether any player participant may be declared a winner for each specified round in the live event.

The exemplary system 200 may include a reward notification device 255 by which, when a participant is determined to have won a prize, award, reward or the like, in the form of, for example, merchandise, discounts, coupons, cash and/or other incentives, the user may be immediately notified. Like the game implementing device 240 above, the reward notification device 255 may be a function of the processor 215, or a stand-alone device, either of which may present reward information user gaming device 280 to be displayed, for example, on a display 289 of the user gaming device 280. The reward notification device 255 may be usable as well to advise an individual player participant as to his or her status as a Super Player substantially in the manner outlined above.

The exemplary system 200 may communicate with one or more user gaming devices 280, each of which may themselves include user interface 281, processor 283, communication interface 285, a memory 287, and a display 289. The user as a player participant in a Squares Game or Super Squares Game may employ a user gaming device 280 for interaction with the exemplary system 200 as it carries into effect the disclosed schemes for implementing the Squares Game or Super Squares Game. It should be noted that one or more of the user gaming devices 280 by which a player participant may participate in the Squares Game or Super Squares Game may be, in addition to the many devices catalogued above, user-wearable I/O and/or computing devices such as, for example, wearable computer/communicating display glasses and/or watches, biometric sensors, virtual reality (or immersion) devices including goggles, helmets, tactile gloves and the like, and other known or developed wearable components for carrying out one or more of computing and/or communicating functions allowing user to communicate with the exemplary system 200.

All of the various components of the exemplary system 200, as depicted in FIG. 2, may be connected internally, and to one or more external components by one or more data/control busses 260. These data/control busses 260 may provide wired or wireless communication between the various components of the exemplary system 200, whether all of the components of the exemplary system 200 are housed integrally in, or are otherwise external and connected to the exemplary system 200.

It should be appreciated that, although depicted in FIG. 2 as an essentially integral unit, the various disclosed elements of the exemplary system 200 may be arranged in any combination of sub-systems as individual components or combinations of components, integral to a single unit, or external to, and in wired or wireless communication with the single unit of the exemplary system 200. Wireless communications may be by RF radio devices, optical interfaces, NFC devices and other wireless communicating devices according to RF, Wi-Fi, WiGig and other like communications protocols. In other words, no specific configuration as an integral unit, or as a support unit, is to be implied by the depiction in FIG. 2. Further, although depicted as individual units for ease of understanding of the details provided in this disclosure regarding the exemplary interface and control system 200, it should be understood that the described functions of any of the individually-depicted components may be undertaken, for example, by one or more processors 215 connected to, and in communication with, one or more data storage device(s) 220.

Figure 3:
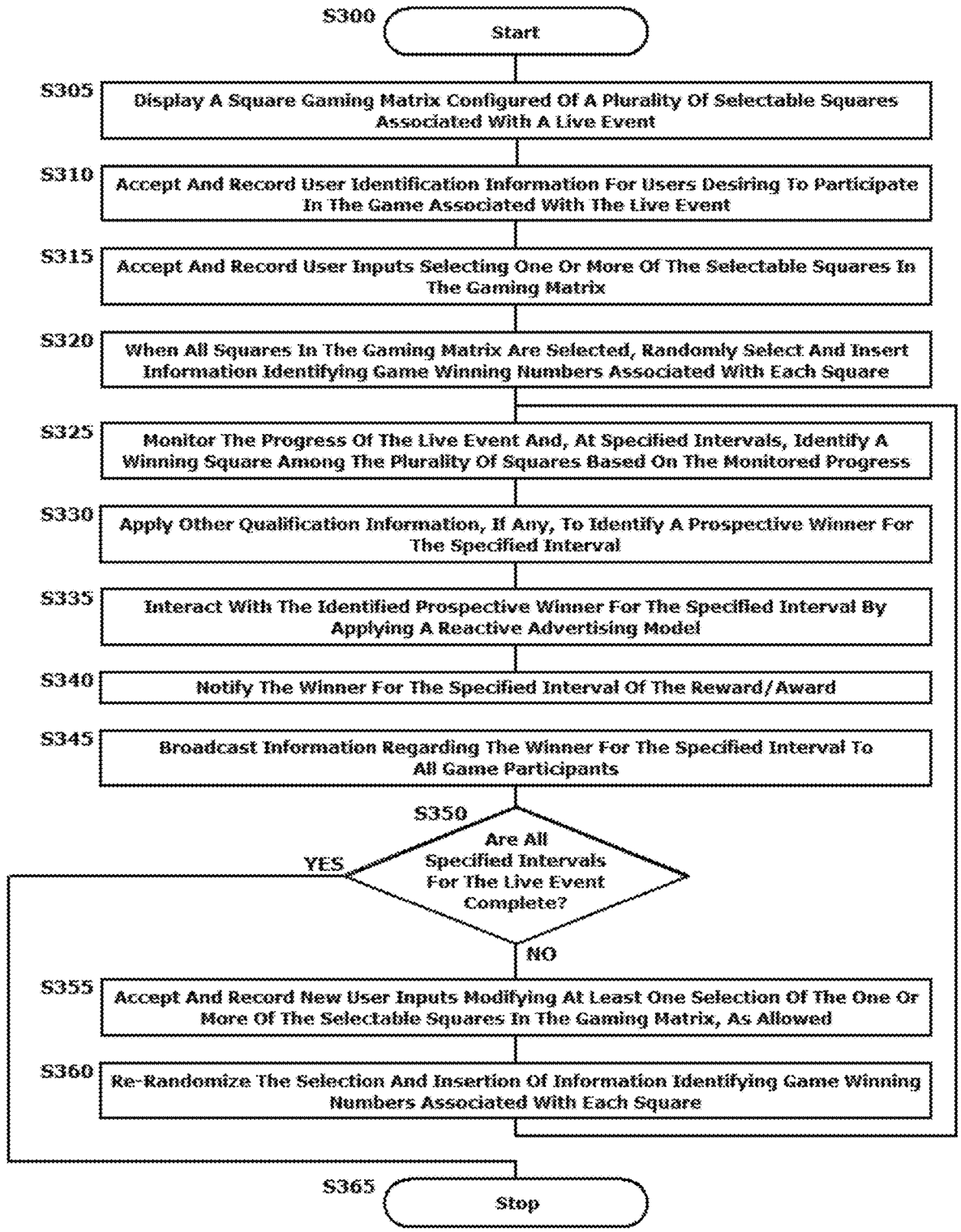
FIG. 3 illustrates a flowchart of a first exemplary method for implementing an advanced automated Squares Game according to this disclosure.

The disclosed embodiments may include exemplary methods for implementing automated Squares Games. FIG. 3 illustrates a flowchart of a first exemplary method. As shown in FIG. 3, operation of the method commences at Step S300 and proceeds to Step S305.

In Step S305, a gaming matrix configured of a plurality of selectable squares associated with a live event may be automatically caused to be displayed. Operation of the method proceeds to Step S310.

In Step S310, player participant identification information for the player participant desiring to participate in the game associated with the live event may be accepted and recorded. Operation of the method proceeds to Step S315.

In Step S315, player participant input selecting one or more of the selectable squares in the gaming matrix may be accepted and recorded. Operation of the method proceeds to Step S320.

In Step S320, when all of the squares in the gaming matrix are selected by, or otherwise identified as being associated with, a player participant, information identifying game-winning numbers associated with each square may be randomly selected and inserted. This process may be automated to replicate the look and feel of a conventional matrix by randomly filling orders squares with selected numbers. Otherwise, the border numbers may be fixed and the individual player participant-selected squares maybe randomized. Operation of the method proceeds to Step S325.

In Step S325, the progress of the live event may be monitored. At specified intervals (rounds), numbers associated with the live event may be extracted to identify a winning square for the specified round among the plurality of squares. This may be the only, or otherwise simply a first, step in identifying a winner of the Squares Game for the specified round. Operation of the method proceeds to Step S330.

In Step S330, other qualification may be applied to identify prospective winner for the specified round. This may include additional qualifying information, or additional random information, or tiebreakers, or identification as a Super Player, or an aggregation and/or leaderboard scheme, or any one or more of the indicated schemes described in detail above. Operation of the method proceeds to Step S335.

In Step S335, a prospective winner may be presented with a reactive advertising scheme in which the prospective winner is presented with advertising content and then asked a series of questions regarding that advertising content. A prospective winner's ability to correctly answer questions based on the reviewed advertising content may be the last step in qualifying the prospective winner as the winner for the specified interval. Operation of the method proceeds to Step S340.

In Step S340, the winner for the specified round may be notified of the reward or award for which the winner has qualified. Additional instructions may be provided, for example, to indicate to the winner how to redeem or otherwise collect the reward or award for which the winner has qualified, or in an accumulated gaming scheme, a leaderboard entry may be provided. Operation of the method proceeds to Step S345.

In Step S345, information regarding the winner for the specified round (or standings on a leaderboard) may be broadcast to all game player participants. Operation of the method proceeds to Step S350.

Step S350 is a determination step in which a determination is made as to whether all of the specified rounds, games, events in a tournament, league events or the like, associated with the Squares Game are complete.

If, in Step S350, a determination is made that all of the specified rounds, games, events in a tournament, league events or the like associated with the Squares Game are complete, operation of the method proceeds to Step S365, where operation of the method ceases.

If, in Step S350, a determination is made that all of the specified rounds, games, events in a tournament, league events or the like associated with the Squares Game are not complete, operation of the method proceeds to Step S355.

In Step S355, player participant inputs modifying at least one selection of the one or more of the selectable squares in the gaming matrix may be accepted and recorded, as allowed. Operation the method proceeds to Step S360.

In Step S360, the selection and insertion of information identifying game-winning numbers associated with each square may be re-randomized. Operation of the method reverts to Step S325.

Figure 4:
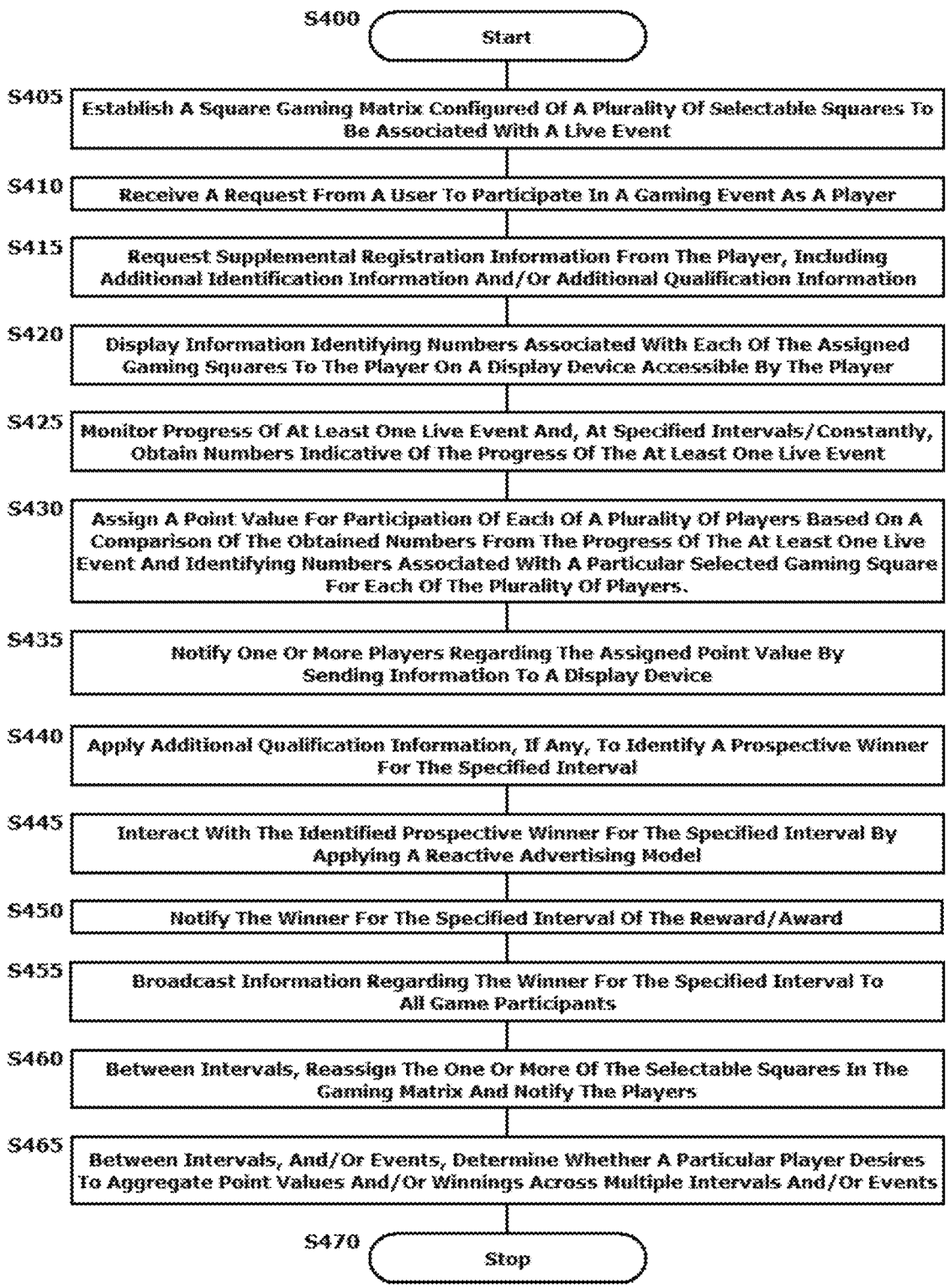
FIG. 4 illustrates a flowchart of a second exemplary method for implementing an advanced automated Squares Game according to this disclosure.

FIG. 4 illustrates a flowchart of a first exemplary method. As shown in FIG. 4, operation of the method commences at Step S400 and proceeds to Step S405.

In Step S405, a gaming matrix configured of a plurality of selectable squares associated with a live event may be established by a system. Operation of the method proceeds to Step S410.

In Step S410, a request from a user to participate in a gaming event as a player may be received. Operation of the method proceeds to Step S415.

In Step S415, supplemental registration information may be read requested and received from the player. Such supplemental registration information may include, for example, information further identifying the player and/or providing some basis for qualification of the player to participate in the gaming event. As an example, a player may be required to complete a reactive advertising scheme including watching a presented advertisement, and responding to a number of queries regarding the content of the presented advertisement. Such information may be used to register the user as a player, and may also be stored for later use, for example, as tiebreaker information. Such information may also include input from the user regarding a number of specific intervals in a particular live event that the user chooses to participate as a player, and/or a number of particular live events in which the user chooses to participate as a player. Operation of the method proceeds to Step S420.

In Step S420, information identifying numbers associated with each of the assigned gaming squares may be displayed to the player on a display device accessible by the player. The display device may be, for example, a common display device in a particular event venue, or it may be a player's own portable mobile computing and/or communicating device, or virtually any other like display device by which information may be presented to the player. Operation of the method proceeds to Step S425.

In Step S425, the progress of the live event may be monitored. Constantly, or at specified intervals (rounds), numbers indicative of the progress of the live event may be obtained. Operation of the method proceeds to Step S430.

In Steps S430, a point value for participation of each of a plurality of players may be assigned based on a comparison of the obtained numbers from the progress of the at least one live event in identifying numbers associated with a particular selected gaming square for each of the plurality of players. An assigned or accumulated point value may represent an only, or otherwise simply a first, step in identifying a winner of the Squares Game during and/or for the specified round. Operation of the method proceeds to Step S435.

In Steps S435, one or more players may be notified regarding the currently-assigned point values based on information being sent to a display device. Operation the method proceeds to Step S440.

In Step S440, additional qualification may be applied to identify prospective winner for the specified round. This may include additional qualifying information, or additional random information, or tiebreakers, or identification as a Super Player, or an aggregation and/or leaderboard scheme, or any one or more of the indicated schemes described in detail above. Operation of the method proceeds to Step S445.

In Step S445, a prospective winner may be presented with a reactive advertising scheme in which the prospective winner is presented with advertising content and then asked a series of questions regarding that advertising content. A prospective winner's ability to correctly answer questions based on the reviewed advertising content may be the last step in qualifying the prospective winner as the winner for the specified interval. Operation of the method proceeds to Step S450.

In Step S450, the winner for the specified round may be notified of the reward or award for which the winner has qualified. Additional instructions may be provided, for example, to indicate to the winner how to redeem or otherwise collect the reward or award for which the winner has qualified, or in an accumulated gaming scheme, a leaderboard entry may be provided. Operation of the method proceeds to Step S455.

In Step S455, information regarding the winner for the specified round (or standings on a leaderboard) may be broadcast to all game player participants. Operation of the method proceeds to Step S460.

In Step S460, the one or more selectable squares in the gaming matrix may be reassigned between intervals, and the players notified. Operation of the method proceeds to Step S465.

In Step S465, a determination may be made between intervals and/or events as to whether a particular player desires to aggregate point values and/or winnings across multiple intervals and/or events. Operation of the method proceeds to Step S470, where operation of the method ceases.

The disclosed embodiments may include a non-transitory computer-readable medium storing instructions which, when executed by a processor may cause the processor to execute all, or at least some, of the steps of the method outlined above.

The above-described exemplary systems and methods reference certain conventional components to provide a brief, general description of suitable operating and presentation scheme implementing environments in which the subject matter of this disclosure may be undertaken for familiarity and ease of understanding. Although not required, embodiments of the disclosure may be provided, at least in part, in a form of hardware circuits, firmware, or software computer-executable instructions to carry out the specific functions described. These may include individual program modules executed by processors.

Those skilled in the art will appreciate that other embodiments of the disclosed subject matter may be practiced in myriad configurations for carrying into effect the disclosed Squares Game schemes with applications hosted on a broad spectrum of computing and communicating devices.

As indicated above, embodiments within the scope of this disclosure may include computer-readable media storing computer-executable instructions or data structures that can be read and executed by one or more processors for controlling the presentation processes for gaming matrices according to the disclosed schemes, and for carrying into effect the overall gaming schemes. Such computer-readable media can comprise RAM, ROM, EEPROM, CD-ROM, flash drives, data memory cards or other analog or digital data storage device that can be used to carry or store desired program elements or steps in the form of accessible computer-executable instructions or data structures.

Computer-executable instructions include, for example, non-transitory instructions and data that can be executed and accessed respectively to cause a processor, for example, in an automated squares game implementing device or system to perform certain of the above-specified data acquisition, game implementation, and display functions. Computer-executable instructions may also include program modules that are remotely stored for access and execution by a processor.

The exemplary depicted sequences of executable instructions or associated data structures represent examples of corresponding sequences of acts for implementing the functions described in the steps of the above-outlined exemplary methods. The exemplary depicted steps may be executed in any reasonable order to carry into effect the objectives of the disclosed embodiments. No particular order to the disclosed steps of the method is necessarily implied by the depiction in FIG. 3 or 4, except where a particular method step is a necessary precondition to execution of any other method step. Separately, not all of the depicted steps of the methods shown in FIGS. 3 and 4 need to be implemented in any particular embodiment.

Although the above description may contain specific details, they should not be construed as limiting the claims in any way. Other configurations of the described embodiments of the disclosed systems and methods are part of the scope of this disclosure. It will be appreciated that various of the above-disclosed and other features and functions, or alternatives thereof, may be desirably combined into many other different systems or applications. Also, various alternatives, modifications, variations or improvements therein may be subsequently made by those skilled in the art which are also intended to be encompassed by the following claims.

I claim:

1. A system for implementing an automated live event related game, comprising:
    a display device that displays information regarding a game matrix including a plurality of selectable gaming squares; and
    a gamification device that is configured to
        receive a request from a user via an information exchange device to participate in a gaming event as a player, the gaming event being associated with at least one live event;
        receive an input from the user as to an outcome of the at least one live event for application as a tie-breaker at the completion of the at least one live event;
        assign one or more selectable gaming squares in the game matrix to each of a plurality of players;
        direct display information identifying numbers associated with each of the assigned gaming squares to the each of the plurality of players on the display device;
        monitor the progress of the at least one live event with which the game matrix is associated;
        automatically obtain numbers indicative of the progress of the at least one live event at a plurality of intervals during the at least one live event;
        automatically assign a point value to participation of each of the plurality of players based on a comparison of the obtained numbers from progress of the at least one live event and the identifying numbers associated with assigned gaming squares for the each of the plurality of players;
        determine prospective winners from among the plurality of players based on a highest accrued point value at the plurality of intervals during the at least one live event and the identifying numbers associated with a particular selected gaming square;
        apply additional winner verification criteria to the prospective winners to determine a final interval winner, the additional winner verification criteria including applying a reactive scheme in which each of the prospective winners is (1) presented with advertising content, (2) presented with a series of queries regarding the advertising content, and (3) required to provide responses to the series of queries that will be evaluated by the gamification device to determine the final interval winner;
        aggregate the final interval winners and apply the input from each of the final interval winners as to the outcome of the at least one live event at the completion of the at least one live event as the tie-breaker between the final interval winners to determine an overall winner; and
        provide notification to each final interval winner and the overall winner by sending information to the display device.

2. The system of claim 1, the gamification device being further configured to
    receive, from a user-controlled electronic device, user identification information; and
    store the received user identification information in a storage device associated with the system.

3. The system of claim 1, the gamification device being further configured to
    re-assign one or more selectable gaming squares in the game matrix to the each of the plurality of players at the completion of one or more of the plurality of intervals during the conduct of the live event; and
    direct display information identifying numbers associated with each of the reassigned gaming squares to the each of the plurality of players on the display device.

4. The system of claim 1, the gamification device being further configured to assign the one or more selectable gaming squares in the game matrix to the each of the plurality of players based on at least one qualification criteria for the each of the plurality of players.

5. The system of claim 1, the gamification device being further configured to
    aggregate assigned point values for the each of the plurality of players across a plurality of live events; and
    provide notification to the plurality of players as to an aggregated points standing for the plurality of players.

6. The system of claim 1, the gamification device being further configured to
    receive, from a user-controlled electronic device, an indication of at least one of a number of intervals in a single live event and a number of separate live events in which a particular player among the plurality of players chooses to participate;
    track the particular player's accumulating aggregate point value across the indicated number of intervals in the single live event and the number of separate live events in which the particular player chooses to participate; and
    provide notification to the particular player as to the aggregate point value accumulated across the indicated number of intervals in the single live event and the number of separate live events in which the particular player chooses to participate by sending information to the user-controlled electronic device of the particular player.

7. A method for implementing an automated live event related game, comprising:
- receiving, with a processor, a request from a user to participate in a gaming event as a player, the gaming event being associated with at least one live event;
- receiving, with the processor, an input from the user as to an outcome of the at least one live event for application as a tie-breaker at the completion of the at least one live event;
- assigning, with the processor, one or more of selectable gaming squares in a game matrix to each of a plurality of players;
- displaying information identifying numbers associated with each of the assigned gaming squares to the each of the plurality of players on the display device;
- monitoring, with the processor, progress of the at least one live event with which the game matrix is associated;
- automatically obtaining, with the processor, numbers indicative of the progress of the live event at a plurality of intervals during the at least one live event;
- automatically assigning, with the processor, a point value for participation of the each of the plurality of players based on a comparison of the obtained numbers from progress of the at least one live event and the identifying numbers associated with assigned gaming square for the each of the plurality of players;
- determining, with the processor, prospective winners from among the plurality of players based on a highest accrued point value at the plurality of intervals during the at least one live event and the identifying numbers associated with a particular selected gaming square;
- applying, with the processor, additional winner verification criteria to the prospective winners to determine a final interval winner, the additional winner verification criteria including applying a reactive scheme in which each of the prospective winners is (1) presented with advertising content, (2) presented with a series of queries regarding the advertising content, and (3) required to provide responses to the series of queries that will be evaluated by the gamification device to determine the final interval winner;
- aggregating the final interval winners;
- applying the input from each of the final interval winners as to the outcome of the at least one live event at the completion of the at least one live event as the tie-breaker between the final interval winners to determine an overall winner; and
- notifying each final interval winner and the overall winner by sending information to the display device.

8. The method of claim 7, further comprising:
- receiving, with the processor from the user-controlled electronic device, user identification information; and
- storing the received user identification information in a storage device associated with the system.

9. The method of claim 7, further comprising:
- re-assigning one or more selectable gaming squares in the game matrix to the each of the plurality of players at the completion one or more of the plurality of intervals during the conduct of the live event; and
- displaying information identifying numbers associated with each of the reassigned gaming squares to the each of the plurality of players on the display device.

10. The method of claim 7, the assigning the one or more selectable gaming squares in the game matrix comprising assigning the one or more selectable gaming squares in the game matrix to the each player based on at least one qualification criteria for the each of the plurality of players.

11. The method of claim 7, further comprising:
- aggregating, with the processor, assigned point values for the each of the plurality of players across a plurality of live events; and
- notifying the plurality of players as to an aggregated points standing for the plurality of players.

12. The method of claim 7, further comprising:
- receiving, with the processor from the user-controlled electronic device, an indication of at least one of a number of intervals in a single live event and a number of separate live events in which a particular player among the plurality of players chooses to participate;
- tracking, with the processor, the particular player's accumulating aggregate point value across the indicated number of intervals in the single live event and the number of separate live events in which the particular player chooses to participate; and
- notifying the particular player as to the aggregate point value accumulated across the indicated number of intervals in the single live event and the number of separate live events in which the particular player chooses to participate by sending information to the user-controlled electronic device of the particular player.

* * * * *